United States Patent
Lange et al.

(10) Patent No.: US 8,083,795 B2
(45) Date of Patent: Dec. 27, 2011

(54) INTERVERTEBRAL PROSTHETIC DEVICE FOR SPINAL STABILIZATION AND METHOD OF MANUFACTURING SAME

(75) Inventors: Eric C. Lange, Collierville, TN (US); Aurelien Bruneau, Memphis, TN (US); Kent M. Anderson, Memphis, TN (US); Thomas Carls, Memphis, TN (US); Jonathan Dewey, Memphis, TN (US); Matthew M. Morrison, Cordova, TN (US); Fred J. Molz, IV, Birmingham, AL (US); Jean Taylor, Cannes (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 128 days.

(21) Appl. No.: 11/334,691

(22) Filed: Jan. 18, 2006

(65) Prior Publication Data
US 2007/0167945 A1    Jul. 19, 2007

(51) Int. Cl.
*A61F 2/44* (2006.01)
(52) U.S. Cl. ............... 623/17.11; 606/248; 606/249
(58) Field of Classification Search ............ 606/61, 606/247–249, 198; 623/17.11–17.16
See application file for complete search history.

(56) References Cited

U.S. PATENT DOCUMENTS

| | | | |
|---|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |

(Continued)

FOREIGN PATENT DOCUMENTS

DE    2821678 A1    11/1979

(Continued)

OTHER PUBLICATIONS

U.S. Appl. No. 11/271,018, filed Nov. 10, 2005, Dewey et al.

(Continued)

*Primary Examiner* — Thomas Barrett
*Assistant Examiner* — Andrew Yang

(57) ABSTRACT

A prosthetic device and method of inserting same between adjacent vertebrae, according to which a first member of a relatively flexible material is adapted to extend between the vertebrae; and at least one second member of a relatively stiff material is supported by the first member.

25 Claims, 4 Drawing Sheets

U.S. PATENT DOCUMENTS

| | | | |
|---|---|---|---|
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,887,596 A | 12/1989 | Sherman |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,946,458 A | 8/1990 | Harms et al. |
| 4,969,887 A | 11/1990 | Sodhi |
| 5,000,166 A | 3/1991 | Karpf |
| 5,002,542 A | 3/1991 | Frigg |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,308 A | 4/1994 | Gross et al. |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove et al. |
| 5,370,697 A | 12/1994 | Baumgartner |
| 5,383,454 A | 1/1995 | Bucholz |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,527,314 A | 6/1996 | Brumfield et al. |
| 5,540,688 A | 7/1996 | Navas |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A * | 7/1997 | Samani ............ 623/17.16 |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,755,798 A | 5/1998 | Papavero et al. |
| 5,800,547 A | 9/1998 | Schafer et al. |
| 5,810,815 A | 9/1998 | Morales |
| 5,827,328 A | 10/1998 | Buttermann |
| 5,836,948 A | 11/1998 | Zucherman et al. |
| 5,849,004 A | 12/1998 | Bramlet |
| 5,851,183 A | 12/1998 | Bucholz |
| 5,860,977 A | 1/1999 | Zucherman et al. |
| 5,871,445 A | 2/1999 | Bucholz |
| 5,888,196 A | 3/1999 | Bonutti |
| 5,891,034 A | 4/1999 | Bucholz |
| 5,919,196 A | 7/1999 | Bobic et al. |
| 5,921,987 A | 7/1999 | Stone |
| 5,941,881 A | 8/1999 | Barnes |
| 5,964,805 A | 10/1999 | Stone |
| 5,976,186 A | 11/1999 | Bao et al. |
| 5,980,523 A | 11/1999 | Jackson |
| 6,004,322 A | 12/1999 | Bernstein |
| 6,007,496 A | 12/1999 | Brannon |
| D420,132 S | 2/2000 | Bucholz et al. |
| 6,021,343 A | 2/2000 | Foley et al. |
| 6,022,376 A | 2/2000 | Assell et al. |
| D422,706 S | 4/2000 | Bucholz et al. |
| 6,048,342 A | 4/2000 | Zucherman et al. |
| 6,059,829 A | 5/2000 | Schläpfer et al. |
| 6,063,090 A | 5/2000 | Schlapfer |
| 6,068,630 A | 5/2000 | Zucherman et al. |
| 6,074,390 A | 6/2000 | Zucherman et al. |
| 6,102,922 A | 8/2000 | Jakobsson et al. |
| 6,110,209 A | 8/2000 | Stone |
| 6,113,638 A | 9/2000 | Williams et al. |
| 6,118,845 A | 9/2000 | Simon et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,143,031 A | 11/2000 | Knothe et al. |
| 6,143,032 A | 11/2000 | Schafer et al. |
| 6,143,033 A | 11/2000 | Paul et al. |
| 6,167,145 A | 12/2000 | Foley et al. |
| 6,179,873 B1 | 1/2001 | Zientek |
| 6,190,395 B1 | 2/2001 | Williams |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,224,631 B1 | 5/2001 | Kohrs |
| 6,226,548 B1 | 5/2001 | Foley et al. |
| 6,235,038 B1 | 5/2001 | Hunter et al. |
| 6,236,875 B1 | 5/2001 | Bucholz et al. |
| 6,245,107 B1 | 6/2001 | Ferree |
| 6,248,105 B1 | 6/2001 | Schlapfer et al. |
| 6,253,210 B1 | 6/2001 | Smith et al. |
| 6,277,149 B1 | 8/2001 | Boyle et al. |
| 6,293,949 B1 | 9/2001 | Justis et al. |
| 6,306,142 B1 | 10/2001 | Johanson et al. |
| 6,325,827 B1 | 12/2001 | Lin |
| 6,336,930 B1 | 1/2002 | Stalcup et al. |
| 6,340,363 B1 | 1/2002 | Bolger et al. |
| 6,348,053 B1 | 2/2002 | Cachia |
| 6,348,058 B1 | 2/2002 | Melkent et al. |
| 6,352,537 B1 | 3/2002 | Strnad |
| 6,364,883 B1 | 4/2002 | Santilli |
| 6,371,957 B1 | 4/2002 | Amrein et al. |
| 6,371,987 B1 | 4/2002 | Weiland et al. |

| | | | | | | |
|---|---|---|---|---|---|---|
| 6,375,658 B1 | 4/2002 | Hangody et al. | | 6,981,975 B2 | 1/2006 | Michelson |
| 6,375,682 B1 | 4/2002 | Fleischmann et al. | | 7,007,699 B2 | 3/2006 | Martinelli et al. |
| 6,379,302 B1 | 4/2002 | Kessman et al. | | 7,011,685 B2 | 3/2006 | Arnin et al. |
| 6,381,485 B1 | 4/2002 | Hunter et al. | | 7,018,415 B1 | 3/2006 | McKay |
| 6,383,221 B1 | 5/2002 | Scarborough et al. | | 7,041,136 B2 | 5/2006 | Goble et al. |
| 6,395,011 B1 | 5/2002 | Johanson et al. | | 7,048,736 B2 | 5/2006 | Robinson et al. |
| 6,402,750 B1 | 6/2002 | Atkinson et al. | | RE39,133 E | 6/2006 | Clayton et al. |
| 6,402,751 B1 | 6/2002 | Hoeck et al. | | 7,070,598 B2 | 7/2006 | Lim et al. |
| 6,402,756 B1 | 6/2002 | Ralph et al. | | 7,081,120 B2 | 7/2006 | Li et al. |
| 6,402,762 B2 | 6/2002 | Hunter et al. | | 7,087,055 B2 | 8/2006 | Lim et al. |
| 6,419,703 B1 | 7/2002 | Fallin et al. | | 7,087,083 B2 | 8/2006 | Pasquet et al. |
| 6,419,704 B1 | 7/2002 | Ferree | | 7,097,648 B1 | 8/2006 | Globerman et al. |
| 6,432,130 B1 | 8/2002 | Hanson | | 7,097,654 B1 | 8/2006 | Freedland |
| 6,434,415 B1 | 8/2002 | Foley et al. | | 7,101,375 B2 | 9/2006 | Zucherman et al. |
| 6,434,507 B1 | 8/2002 | Clayton et al. | | 7,163,558 B2 | 1/2007 | Senegas et al. |
| 6,436,140 B1 | 8/2002 | Liu et al. | | 7,186,254 B2 | 3/2007 | Dinh et al. |
| 6,440,141 B1 | 8/2002 | Philippon | | 7,201,751 B2 | 4/2007 | Zucherman et al. |
| 6,440,169 B1 | 8/2002 | Elberg et al. | | 7,217,293 B2 | 5/2007 | Branch, Jr. |
| 6,447,513 B1 | 9/2002 | Griggs | | 7,238,204 B2 | 7/2007 | Le Couedic et al. |
| 6,451,019 B1 | 9/2002 | Zucherman et al. | | 7,306,628 B2 | 12/2007 | Zucherman et al. |
| 6,470,207 B1 | 10/2002 | Simon et al. | | 7,335,203 B2 | 2/2008 | Winslow et al. |
| 6,474,341 B1 | 11/2002 | Hunter et al. | | 7,377,942 B2 | 5/2008 | Berry |
| 6,488,033 B1 | 12/2002 | Cerundolo | | 7,431,735 B2 | 10/2008 | Liu et al. |
| 6,490,467 B1 | 12/2002 | Bucholz et al. | | 7,442,208 B2 | 10/2008 | Mathieu et al. |
| 6,491,699 B1 | 12/2002 | Henderson et al. | | 7,445,637 B2 | 11/2008 | Taylor |
| 6,500,178 B2 | 12/2002 | Zucherman et al. | | 7,458,981 B2 | 12/2008 | Fielding et al. |
| 6,503,279 B1 | 1/2003 | Webb et al. | | 7,582,106 B2 | 9/2009 | Teitelbaum et al. |
| 6,511,508 B1 | 1/2003 | Shahinpoor et al. | | 7,604,652 B2 | 10/2009 | Arnin et al. |
| 6,514,256 B2 | 2/2003 | Zucherman et al. | | 7,611,316 B2 | 11/2009 | Panasik et al. |
| 6,520,963 B1 | 2/2003 | McKinley | | 7,621,950 B1 | 11/2009 | Globerman et al. |
| 6,520,991 B2 | 2/2003 | Huene | | 7,658,752 B2 | 2/2010 | Labrom et al. |
| 6,530,955 B2 | 3/2003 | Boyle et al. | | 7,749,252 B2 | 7/2010 | Zucherman et al. |
| 6,535,756 B1 | 3/2003 | Simon et al. | | 7,771,456 B2 | 8/2010 | Hartmann et al. |
| 6,540,668 B1 | 4/2003 | Schulz et al. | | 7,862,615 B2 | 1/2011 | Carli et al. |
| 6,547,823 B2 | 4/2003 | Scarborough et al. | | 7,901,430 B2 | 3/2011 | Matsuura et al. |
| 6,553,152 B1 | 4/2003 | Miller et al. | | 7,927,354 B2 | 4/2011 | Edidin et al. |
| 6,554,833 B2 | 4/2003 | Levy | | 2001/0016743 A1 | 8/2001 | Zucherman et al. |
| 6,565,605 B2 | 5/2003 | Goble et al. | | 2002/0128716 A1 | 9/2002 | Cohen et al. |
| 6,582,433 B2 | 6/2003 | Yun | | 2002/0143331 A1 | 10/2002 | Zucherman et al. |
| 6,582,467 B1 | 6/2003 | Teitelbaum et al. | | 2003/0040746 A1 | 2/2003 | Mitchell et al. |
| 6,592,585 B2 | 7/2003 | Lee et al. | | 2003/0045940 A1 | 3/2003 | Eberlein et al. |
| 6,592,588 B1 | 7/2003 | Bobic et al. | | 2003/0065330 A1 | 4/2003 | Zucherman et al. |
| 6,613,090 B2 | 9/2003 | Fuss et al. | | 2003/0153915 A1 | 8/2003 | Nekozuka et al. |
| 6,626,944 B1 | 9/2003 | Taylor | | 2003/0176925 A1 | 9/2003 | Paponneau |
| 6,636,757 B1 | 10/2003 | Jascob et al. | | 2004/0010312 A1 | 1/2004 | Enayati |
| 6,645,207 B2 | 11/2003 | Dixon et al. | | 2004/0010316 A1 | 1/2004 | William et al. |
| 6,663,635 B2 | 12/2003 | Frigg et al. | | 2004/0034437 A1 | 2/2004 | Schmieding |
| 6,669,635 B2 | 12/2003 | Kessman et al. | | 2004/0039400 A1 | 2/2004 | Schmieding et al. |
| 6,669,729 B2 | 12/2003 | Chin | | 2004/0059425 A1 | 3/2004 | Schmieding |
| 6,685,742 B1 | 2/2004 | Jackson | | 2004/0064094 A1 | 4/2004 | Freyman |
| 6,695,842 B2 | 2/2004 | Zucherman et al. | | 2004/0087947 A1 | 5/2004 | Lim et al. |
| 6,699,246 B2 | 3/2004 | Zucherman et al. | | 2004/0092939 A1 | 5/2004 | Freid et al. |
| 6,706,067 B2 | 3/2004 | Shimp et al. | | 2004/0097931 A1 | 5/2004 | Mitchell |
| 6,708,184 B2 | 3/2004 | Smith et al. | | 2004/0106995 A1 | 6/2004 | Le Couedic et al. |
| 6,709,435 B2 | 3/2004 | Lin | | 2004/0117017 A1 | 6/2004 | Pasquet et al. |
| 6,723,126 B1 | 4/2004 | Berry | | 2004/0133204 A1 | 7/2004 | Davies |
| 6,725,080 B2 | 4/2004 | Melkent et al. | | 2004/0133280 A1 | 7/2004 | Trieu |
| 6,730,126 B2 | 5/2004 | Boehm, Jr. et al. | | 2004/0158248 A1 | 8/2004 | Ginn |
| 6,733,531 B1 | 5/2004 | Trieu | | 2004/0167625 A1 | 8/2004 | Beyar et al. |
| 6,733,534 B2 | 5/2004 | Sherman | | 2004/0172029 A1 | 9/2004 | Lerch |
| 6,736,818 B2 | 5/2004 | Perren et al. | | 2004/0176771 A1 | 9/2004 | Schmieding |
| 6,743,257 B2 | 6/2004 | Castro | | 2004/0186577 A1 | 9/2004 | Ferree |
| 6,754,374 B1 | 6/2004 | Miller et al. | | 2004/0193154 A1 | 9/2004 | Leatherbury et al. |
| 6,758,863 B2 | 7/2004 | Estes et al. | | 2004/0199255 A1* | 10/2004 | Mathieu et al. ............ 623/17.11 |
| 6,761,720 B1 | 7/2004 | Senegas | | 2004/0260397 A1 | 12/2004 | Lambrecht et al. |
| 6,767,354 B2 | 7/2004 | Johanson et al. | | 2005/0010293 A1 | 1/2005 | Zucherman et al. |
| 6,770,096 B2 | 8/2004 | Bolger et al. | | 2005/0033434 A1* | 2/2005 | Berry ....................... 623/17.14 |
| 6,783,530 B1 | 8/2004 | Levy | | 2005/0049590 A1 | 3/2005 | Alleyne et al. |
| 6,796,988 B2 | 9/2004 | Melkent et al. | | 2005/0049708 A1 | 3/2005 | Atkinson et al. |
| 6,835,205 B2 | 12/2004 | Atkinson et al. | | 2005/0056292 A1 | 3/2005 | Cooper |
| 6,843,805 B2 | 1/2005 | Webb et al. | | 2005/0085814 A1 | 4/2005 | Sherman et al. |
| 6,852,114 B2 | 2/2005 | Cerundolo | | 2005/0101962 A1 | 5/2005 | Schwenke et al. |
| 6,892,090 B2 | 5/2005 | Verard et al. | | 2005/0125061 A1 | 6/2005 | Zucherman |
| 6,902,580 B2 | 6/2005 | Fallin et al. | | 2005/0143827 A1 | 6/2005 | Globerman et al. |
| 6,905,512 B2 | 6/2005 | Paes et al. | | 2005/0165398 A1 | 7/2005 | Reiley |
| 6,920,347 B2 | 7/2005 | Simon et al. | | 2005/0203512 A1 | 9/2005 | Hawkins |
| 6,932,820 B2 | 8/2005 | Osman | | 2005/0203519 A1 | 9/2005 | Harms et al. |
| 6,946,000 B2 | 9/2005 | Senegas et al. | | 2005/0203624 A1 | 9/2005 | Serhan et al. |
| 6,978,166 B2 | 12/2005 | Foley et al. | | 2005/0222687 A1 | 10/2005 | Vunjak-Novakovic et al. |

| | | | |
|---|---|---|---|
| 2005/0228391 A1 | 10/2005 | Levy et al. | |
| 2005/0245929 A1 | 11/2005 | Winslow | |
| 2005/0245937 A1 | 11/2005 | Winslow | |
| 2005/0261768 A1* | 11/2005 | Trieu | 623/17.11 |
| 2005/0267579 A1 | 12/2005 | Reiley et al. | |
| 2005/0273166 A1 | 12/2005 | Sweeney | |
| 2005/0288672 A1 | 12/2005 | Feree | |
| 2006/0004447 A1 | 1/2006 | Mastrorio et al. | |
| 2006/0004455 A1 | 1/2006 | Leonard et al. | |
| 2006/0015181 A1 | 1/2006 | Elberg | |
| 2006/0015183 A1 | 1/2006 | Gilbert et al. | |
| 2006/0047282 A1 | 3/2006 | Gordon | |
| 2006/0060209 A1 | 3/2006 | Shepard | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089718 A1* | 4/2006 | Zucherman et al. | 623/17.11 |
| 2006/0089719 A1 | 4/2006 | Trieu | |
| 2006/0095136 A1 | 5/2006 | McLuen | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0116690 A1 | 6/2006 | Pagano | |
| 2006/0122620 A1 | 6/2006 | Kim | |
| 2006/0129239 A1 | 6/2006 | Kwak | |
| 2006/0136060 A1 | 6/2006 | Taylor | |
| 2006/0142858 A1 | 6/2006 | Colleran et al. | |
| 2006/0149242 A1 | 7/2006 | Kraus et al. | |
| 2006/0182515 A1 | 8/2006 | Panasik et al. | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0224159 A1 | 10/2006 | Anderson | |
| 2006/0224241 A1 | 10/2006 | Butler et al. | |
| 2006/0235387 A1 | 10/2006 | Peterman | |
| 2006/0235532 A1 | 10/2006 | Meunier et al. | |
| 2006/0241601 A1 | 10/2006 | Trautwein et al. | |
| 2006/0241613 A1 | 10/2006 | Brueneau et al. | |
| 2006/0241643 A1 | 10/2006 | Lim et al. | |
| 2006/0241757 A1 | 10/2006 | Anderson | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0282075 A1 | 12/2006 | Labrom et al. | |
| 2006/0282079 A1 | 12/2006 | Labrom et al. | |
| 2006/0293662 A1 | 12/2006 | Boyer, II et al. | |
| 2006/0293663 A1 | 12/2006 | Walkenhorst et al. | |
| 2007/0005064 A1 | 1/2007 | Anderson et al. | |
| 2007/0010813 A1 | 1/2007 | Zucherman et al. | |
| 2007/0032790 A1 | 2/2007 | Aschmann et al. | |
| 2007/0043362 A1 | 2/2007 | Malandain et al. | |
| 2007/0043363 A1 | 2/2007 | Malandain et al. | |
| 2007/0049935 A1 | 3/2007 | Edidin et al. | |
| 2007/0073289 A1 | 3/2007 | Kwak et al. | |
| 2007/0100340 A1 | 5/2007 | Lange et al. | |
| 2007/0123861 A1 | 5/2007 | Dewey et al. | |
| 2007/0142915 A1 | 6/2007 | Altarac et al. | |
| 2007/0151116 A1 | 7/2007 | Malandain | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0191838 A1 | 8/2007 | Bruneau et al. | |
| 2007/0198091 A1 | 8/2007 | Boyer et al. | |
| 2007/0225807 A1 | 9/2007 | Phan et al. | |
| 2007/0225810 A1 | 9/2007 | Colleran et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0097446 A1 | 4/2008 | Reiley et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0177306 A1 | 7/2008 | Lamborne et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0099610 A1 | 4/2009 | Johnson et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2009/0292316 A1 | 11/2009 | Hess | |
| 2009/0326538 A1 | 12/2009 | Sennett et al. | |
| 2010/0121379 A1 | 5/2010 | Edmond | |
| 2010/0191241 A1 | 7/2010 | McCormack et al. | |
| 2010/0204732 A1 | 8/2010 | Aschmann et al. | |
| 2010/0211101 A1 | 8/2010 | Blackwell et al. | |

FOREIGN PATENT DOCUMENTS

| | | |
|---|---|---|
| DE | 3922044 A1 | 2/1991 |
| DE | 4012622 | 7/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 | 10/2001 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |

| | | | |
|---|---|---|---|
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 | 4/2001 |
| FR | 2799948 A1 | 4/2001 |
| FR | 2816197 A1 | 5/2002 |
| FR | 2858929 | 2/2005 |
| JP | 02-224660 | 9/1990 |
| JP | 09-075381 | 3/1997 |
| JP | 2003-079649 | 3/2003 |
| JP | 2003079649 | 3/2003 |
| SU | 988281 | 1/1983 |
| SU | 1484348 A1 | 6/1989 |
| SU | 1484348 | 7/1989 |
| WO | 92/01428 | 2/1992 |
| WO | 94/24933 | 11/1994 |
| WO | WO 94/26192 | 11/1994 |
| WO | WO 94/26195 | 11/1994 |
| WO | 96/11624 | 4/1996 |
| WO | 97/18769 | 5/1997 |
| WO | 98/22050 | 5/1998 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | 02/051326 | 7/2002 |
| WO | 03/015645 | 2/2003 |
| WO | WO 03/057055 A1 | 7/2003 |
| WO | WO 2004/110300 A2 | 2/2004 |
| WO | 2004/024010 | 3/2004 |
| WO | 2004/026188 | 4/2004 |
| WO | WO 2004/047689 A1 | 6/2004 |
| WO | WO 2004/047691 A1 | 6/2004 |
| WO | 2004/084743 A1 | 10/2004 |
| WO | 2004/084768 A2 | 10/2004 |
| WO | 2005/009300 | 2/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | 2005/115261 | 12/2005 |
| WO | 2006/064356 A1 | 6/2006 |
| WO | 2007/001994 | 1/2007 |
| WO | WO 2007/034516 A1 | 3/2007 |
| WO | 2007052975 A1 | 5/2007 |
| WO | WO2007052975 A | 5/2007 |
| WO | 2009/083583 A1 | 7/2009 |
| WO | WO 2009/083276 A1 | 7/2009 |
| WO | 2009/098536 A1 | 8/2009 |

OTHER PUBLICATIONS

U.S. Appl. No. 11/261,386, filed Oct. 27, 2005, Lange et al.
U.S. Appl. No. 11/167,775, filed Jun. 27, 2005, Anderson et al.
U.S. Appl. No. 11/095,215, filed Mar. 31, 2005, Anderson.
U.S. Appl. No. 11/095,214, filed Mar. 31, 2005, Anderson.
European Patent Office, International Searching Authority, Notification of Transmittal of the International Search Report and the Written Opinion of the International Searching Authority or the Declaration, International Application No. PCT/US2007/062405, Aug. 2, 2007, 9 pages.
Unpublished U.S. Appl. No. 11/508,349, filed Aug. 23, 2006 titled "Method and Apparatus for Osteochondral Autograft Transplantation".
Unpublished U.S. Appl. No. 11/514,433, filed Sep. 1, 2006 titled "Improved Osteochondral Implant Procedure".
Unpublished U.S. Appl. No. 11/551,979, filed Oct. 23, 2006 titled "Method and Apparatus for Osteochondral Autograft Transplantation".
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology" Spine, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," Spine, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," Spine, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Anthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. 1.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp.1-7.

Buric et al., "DIAM Device For Low Back Pain In Degenerative Disc Disease 24 Months Follow-up." Advances in Minimally Invasive Surgery And Therapy For Spine and Nerves, Alexandre et al., eds., 2011, pp. 177-182, Spinger-Verlat/Wien.

Phillips et al "Biomechanics of Posterior Dynamic Stabilizing Device (DIAM) After Facetectomy and Discectomy," The Spine Journal, 2006, vol. 6, pp, 714-722.

Taylor et al., "Device For Intervertebral Assisted Motion: Technique and Initial Results," Neurosurg. Focus, Jan. 2007, vol. 22, No. 1, pp. 1-6.

Wilke et al., "Biomechanical Effect of Different Lumbar Interspinous Implants on Flexibility and Intradiscal Pressure," Eur. Spine J., vol. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner

INTERVERTEBRAL PROSTHETIC DEVICE FOR SPINAL STABILIZATION AND METHOD OF MANUFACTURING SAME

BACKGROUND

The present invention relates to an intervertebral prosthetic device for stabilizing the human spine.

Spinal discs that extend between adjacent vertebrae in vertebral columns of the human body provide critical support between the adjacent vertebrae. These discs can rupture, degenerate, and/or protrude by injury, degradation, disease, or the like to such a degree that the intervertebral space between adjacent vertebrae collapses as the disc loses at least a part of its support function, which can cause impingement of the nerve roots and severe pain.

In these cases, intervertebral prosthetic devices have been designed that can be implanted between the adjacent vertebrae, both anterior and posterior of the column, to prevent the collapse of the intervertebral space between the adjacent vertebrae and thus stabilize the spine.

However, many of these devices are relatively stiff, and, as such, cannot flex to better accommodate the vertebrae and do not provide a sufficient amount of shock absorption. Also, many of these devices, when implanted, suffer from a relatively high fatigue.

SUMMARY

The intervertebral prosthetic device according to the embodiments of the invention overcomes the above deficiencies by providing relatively high shock absorption, as well as a good fit with the anatomy and relatively low fatigue characteristics.

Various embodiments of the invention may possess one or more of the above features and advantages, or provide one or more solutions to the above problems existing in the prior art.

DETAILED DESCRIPTION

Figure 1:
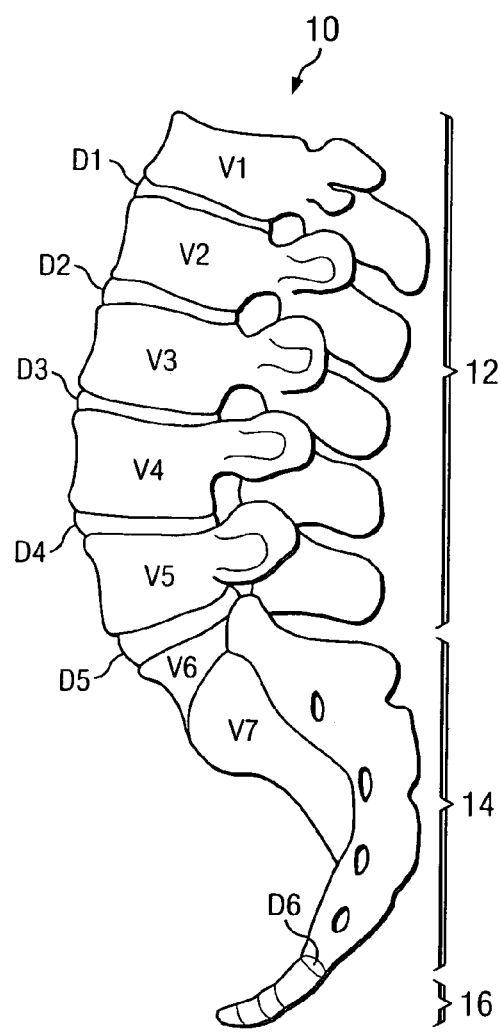
FIG. 1 is a side elevational view of an adult human vertebral column.
Figure 2:
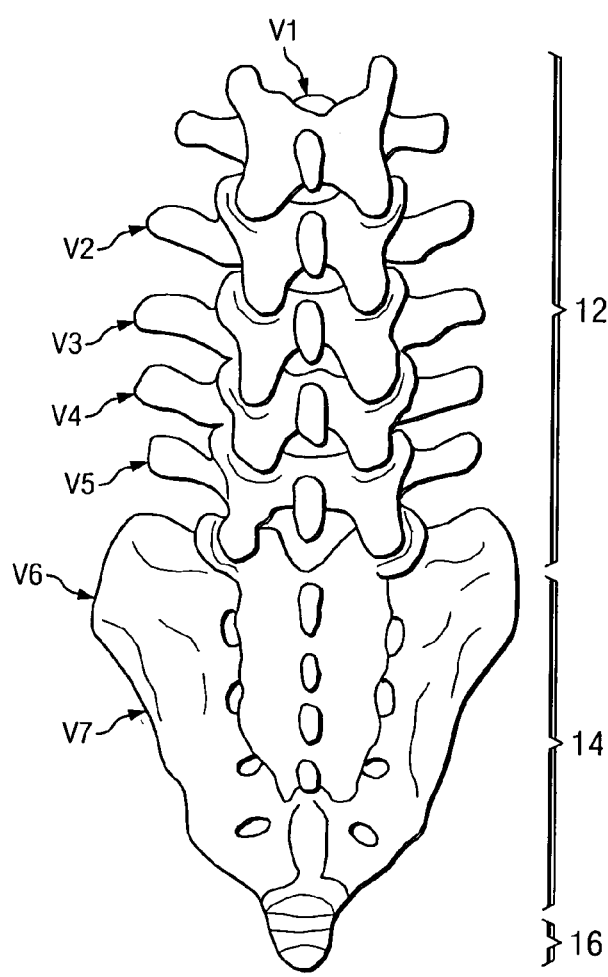
FIG. 2 is a posterior elevational view of the column of FIG. 1.

With reference to FIGS. 1 and 2, the reference numeral 10 refers, in general, to an human vertebral column 10. The lower portion of the vertebral column 10 is shown and includes the lumbar region 12, the sacrum 14, and the coccyx 16. The flexible, soft portion of the vertebral column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The sacrum 14 includes five fused vertebrae, one of which is a superior vertebrae V6 separated from the vertebrae V5 by a disc D5. The other four fused vertebrae of the sacrum 14 are referred to collectively as V7. A disc D6 separates the sacrum 14 from the coccyx 16 which includes four fused vertebrae (not referenced).

Figure 3:
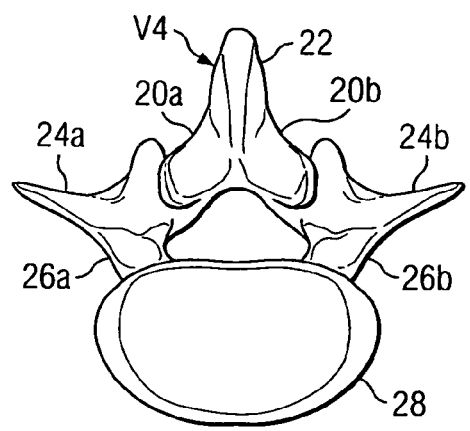
FIG. 3 is an enlarged, front elevational view of one of the vertebrae of the column of FIGS. 1 and 2.

With reference to FIG. 3, the vertebrae V4 includes two laminae 20a and 20b extending to either side (as viewed in FIG. 2) of a spinous process 22 that projects posteriorly from the juncture of the two laminae. Two transverse processes 24a and 24b extend laterally from the laminae 20a and 20b, respectively, and two pedicles 26a and 26b extend inferiorly from the processes 24a and 24b to a vertebral body 28. Since the other vertebrae V1-V3 and V5 are similar to the vertebrae V4 they will not be described in detail.

Figure 4:
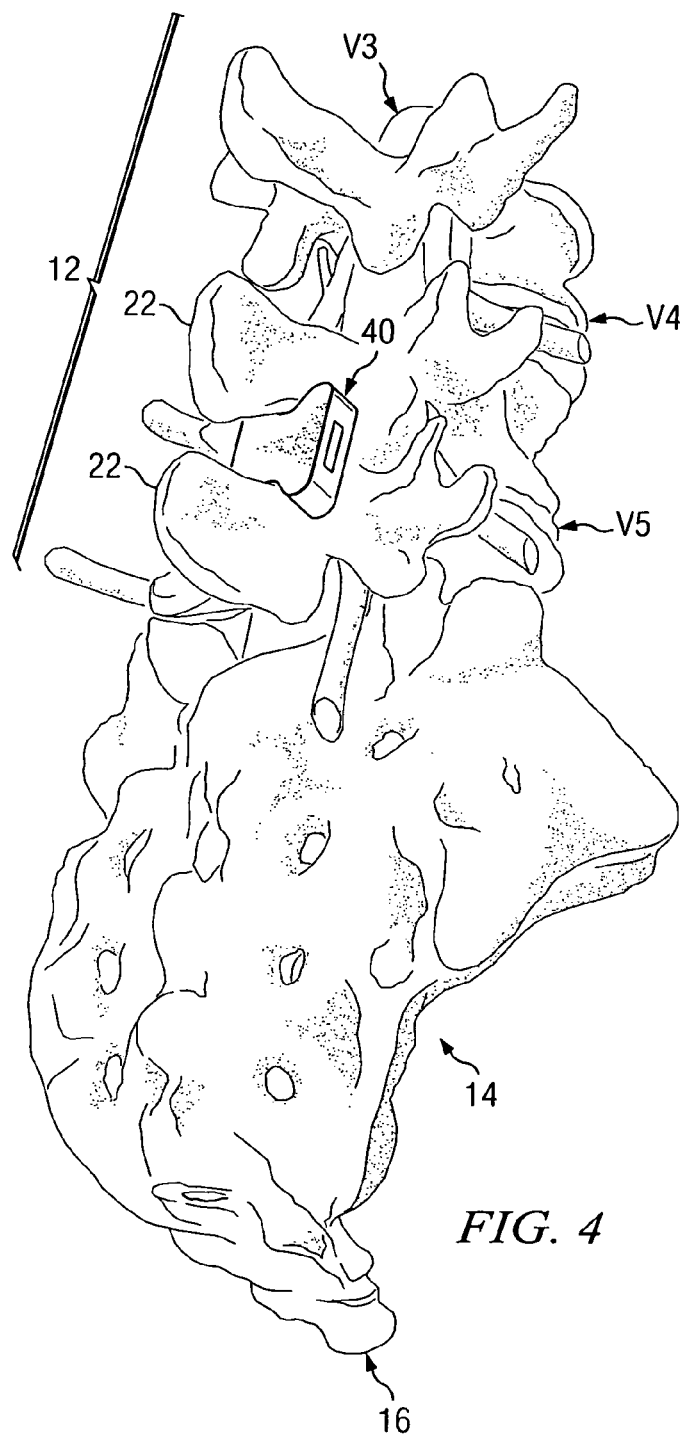
FIG. 4 is an enlarged, partial, isometric view of a portion of the column of FIGS. 1 and 2, including the lower three vertebrae of the column, and depicting the intervertebral prosthetic device according to an embodiment of the invention inserted between two adjacent vertebrae.

Referring to FIG. 4, it will be assumed that, for one or more of the reasons set forth above, the vertebrae V4 and V5 are not being adequately supported by the disc D4 and that it is therefore necessary to provide supplemental support and stabilization of these vertebrae. To this end, an intervertebral disc prosthetic device 40 according to an embodiment of the invention is implanted between the spinous processes 22 of the vertebrae V4 and V5.

Figure 5:
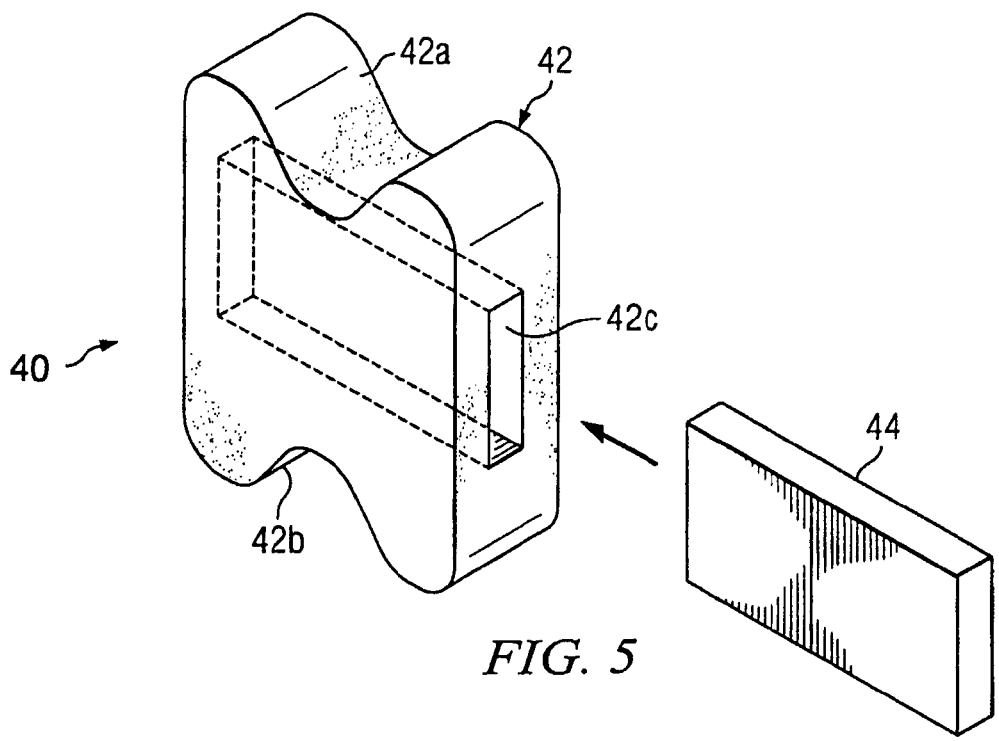
FIG. 5 is an enlarged, isometric, exploded view of the prosthetic device of FIG. 4.

The prosthetic device 40 is shown in detail in FIG. 5 and includes a relatively flexible, soft, body member 42 which is substantially rectangular in shape with the exception that two curved notches 42a and 42b are formed its respective end portions. A laterally extending channel 42c, having a substantially rectangular cross section, extends through the entire width of the body member 42 approximately midway between the notches 42a and 42b.

An insert 44, of a relatively stiff material, is provided that is dimensioned so as to extend in the channel 42c with minimum clearance. Thus, the insert 44 has a substantially rectangular cross-section that substantially corresponds to that of the channel 42c, with the exception that it is slightly smaller so as to fit in the channel. The length of the insert 44 substantially corresponds to the length of the channel 42c.

When the device 40 is implanted between the two adjacent vertebrae V4 and V5 (FIG. 4), the spinous process 22 of one of the vertebrae V4 or V5 extends in the notch 42a and the spinous process of the other vertebrae extends in the notch 42b. The relatively flexible, soft body member 42 provides excellent shock absorption, and the insert 44 adds stiffness, compressive strength and durability to the device 40.

It is understood that the surgeon could be provided with several inserts 44 that vary in stiffness. Thus, once the surgeon ascertains the condition of the vertebrae V4 and V5 (FIG. 4) and determines the particular stiffness that is needed, the proper insert 44 can be selected.

Figure 6:
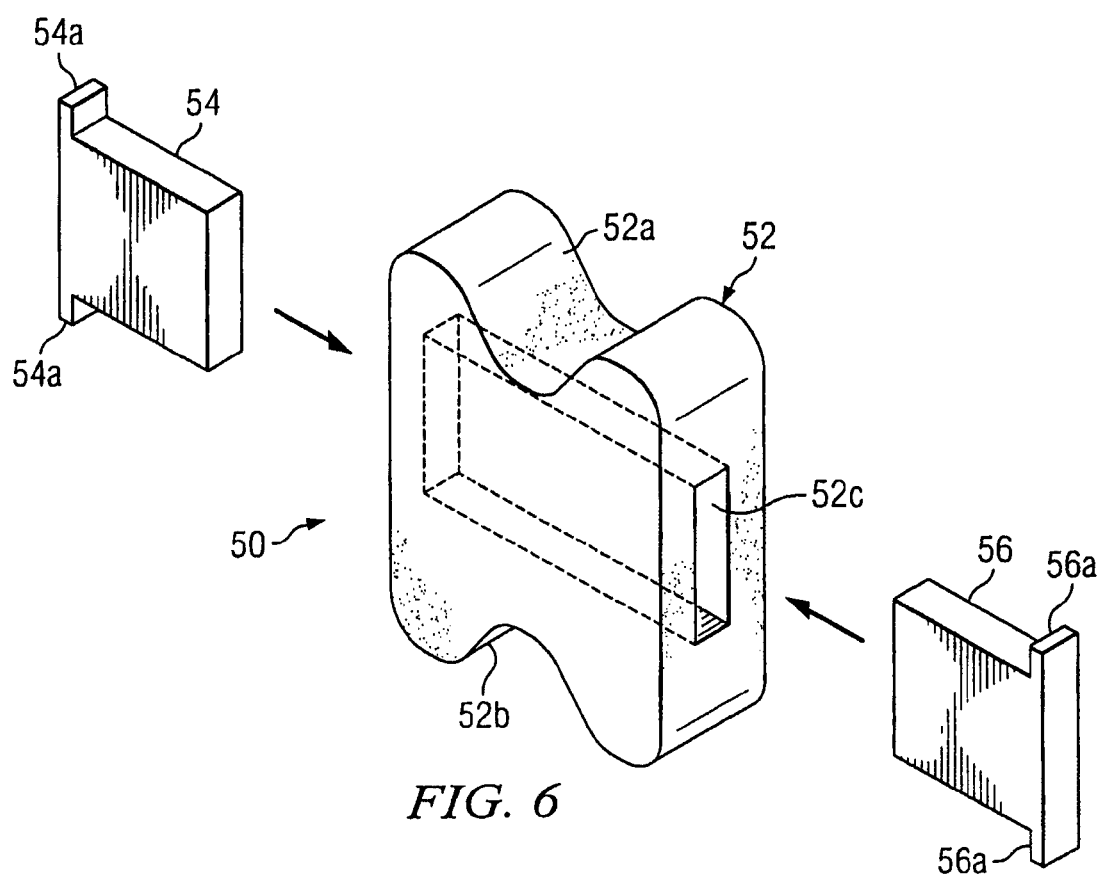
FIGS. 6 and 7 are enlarged, isometric, exploded views of alternate embodiments of the prosthetic device of FIG. 5.

A prosthetic device 50 according to another embodiment is shown in detail in FIG. 6 and includes a relatively flexible, soft body member 52 which is substantially rectangular in shape with the exception that two curved notches 52a and 52b are formed in its respective end portions, as viewed in the drawing. A laterally extending channel 52c, having a substantially rectangular cross section, extends through the body member 52.

Two inserts 54 and 56, of a relatively stiff material, are provided and each is dimensioned so as to extend in the channel 52c with minimum clearance. Each insert 54 and 56 has a substantially rectangular cross section that substantially corresponds to that of the channel 52c, with the exception that the inserts are slightly smaller than the channel so as to fit in the channel. The outer ends of the inserts 54 and 56 are provided with outwardly extending flanges 54a and 56a, respectively.

The inserts 54 and 56 are inserted into the channel 52c from opposite sides in the directions shown by the arrows in FIG. 6, until the flanges 54a and 56a engage the corresponding outer surfaces of the body member 52 to limit the extension of the inserts into the channel. In the inserted positions of the inserts 54 and 56, their combined length substantially corresponds to the length of the channel 52c.

When the device 50 is implanted between the two adjacent vertebrae V4 and V5 (FIG. 4), the spinous process 22 of one of the vertebrae V4 or V5 extends in the notch 52a and the spinous process of the other vertebrae extends in the notch 52b. The relatively flexible, soft body member 52 provides excellent shock absorption, and the inserts 54 and 56 add stiffness, compressive strength and durability to the device 50.

It is understood that the surgeon could be provided with several pairs of inserts 54 and 56 that vary in stiffness from pair to pair. Thus, once the surgeon ascertains the condition of the vertebrae V4 and V5 (FIG. 4) and determines the particular stiffness that is needed, the proper inserts 54 and 56 can be selected.

Figure 7:
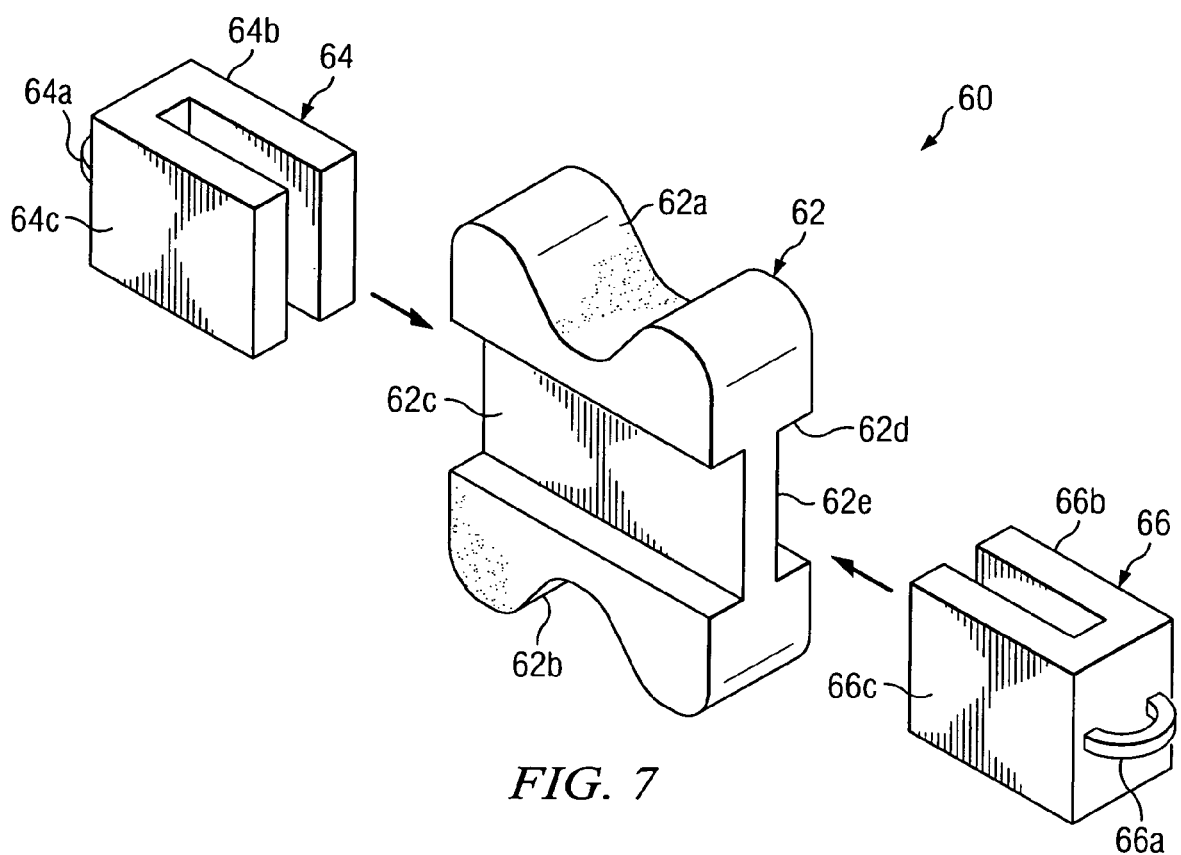

A prosthetic device 60 according to another embodiment is shown in detail in FIG. 7 and includes a relatively flexible, soft body member 62 which is substantially rectangular in shape with the exception that two curved notches 62a and 62b are formed in its respective end portions, as viewed in the drawing.

A groove 62c is formed in the front face of the body member 62, as viewed in the drawing, and extends across its width approximately mid-way between the notches 62a and 62b. A groove 62d is formed in the rear face of the body member 62 and also extends across its width approximately mid-way between the notches 62a and 62b. The grooves 62c and 62d thus define a center portion 62e of the body member 62 that has a reduced thickness.

Two substantially U-shaped inserts 64 and 66, of a relatively stiff material, are provided. The insert 64 is formed by a base 64a from which two spaced legs 64b and 64c extend at right angles, and the insert 66 is formed by a base 66a from which two spaced legs 66b and 66c extend at right angles. The thicknesses of the legs 64b and 64c of the insert 64 substantially correspond to the depth of the notches 62c and 62d, respectively, the lengths of the legs substantially correspond to one-half the length of the notches, and the space between the legs substantially correspond to the thickness of the center portion 62e. Similarly, the thicknesses of the legs 66b and 66c of the insert 66 substantially correspond to the depth of the notches 62c and 62d, respectively. The lengths of the legs substantially correspond to one-half the length of the notches, and the space between the legs substantially correspond to the thickness of the center portion 62e. Thus, when the inserts 64 and 66 are inserted in the grooves 62c and 62d, each extends over approximately one-half of the center portion 62e of the body member 62.

An extrusion 68a and 68b extend from the outer surfaces of the each base 64a and 66b, respectively, for tethering the bases to the vertebrae V4 and V5 (FIG. 4).

The inserts 64 and 66 are inserted into the groove 62c from opposite sides in the directions shown by the arrows in FIG. 7 until their respective bases 64a and 66b engage the corresponding side walls of the center portion 62d. In this inserted position, the combined lengths of the inserts 64 and 66 substantially correspond to the length of the groove 62c.

When the device 60 is implanted between the two adjacent vertebrae V4 and V5 (FIG. 4), the spinous process 22 of one of the vertebrae V4 or V5 extends in the notch 62a and the spinous process of the other vertebrae extends in the notch 62b. The extrusions 68a and 68b are used to tether the device 60 to the spinous processes 22.

The relatively flexible, soft body member 62 provides excellent shock absorption, and the inserts 64 and 66 add stiffness, compressive strength and durability to the device 60.

It is understood that the surgeon could be provided with several pair of inserts 64 and 66 that vary in stiffness from pair to pair. Thus, once the surgeon ascertains the condition of the vertebrae V4 and V5 (FIG. 4) and determines the particular stiffness that is needed, the proper inserts 64 and 66 can be selected.

It is understood that, in each of the above embodiments, the material making up the body members 42, 52, 62, 72 74, 82, 92, and 94 can be of a flexible, soft plastic, such as silicon, which can be molded into the shapes shown and described. The inserts 44, 54, 56, 64, 66, as well as the connectors 76 and 96 and the body member 84 can be of a relatively stiff rubber, plastic, metal, or other similar material.

Variations

It is understood that variations may be made in the foregoing without departing from the invention and examples of some variations are as follows:

Any conventional substance that promotes bone growth, such as HA coating, BMP, or the like, can be incorporated in each of the above embodiments The relatively stiff components of the above devices may have through holes formed therein to improve integration of the bone growth.

The body members, inserts, and connectors of one or more of the above embodiments may vary in shape, size, composition, and physical properties. For example the insert 44 of the embodiment of FIG. 5 can be circular in cross section.

Through openings can be provided through one or more components of each of the above embodiments to receive tethers for attaching the devices to the vertebrae or to a spinous processes.

The insert 44 of the embodiment of FIG. 5 can be secured in the channel 42c of the body member 40 in any conventional manner.

The inserts 54 and 56 of the embodiment of FIG. 6 can be secured in the channel 52c of the body member 50 in any conventional manner.

The bilateral extrusions, shown in the embodiment of FIG. 7, may be provided on the relative stiff component of each embodiment for tethering the device to a vertebrae or a spinous process.

The relative stiff components described above could be made of a resorbable material so that their stiffness would change over time.

The inserts 64 and 66 of the embodiment of FIG. 7 can be secured in the channel 62c of the body member 60 in any conventional manner.

The relatively stiff components described above could be replaced by components having a different stiffness pre-operatively or intra-operatively.

In each of the above embodiments, the components that are made of a relatively flexible, soft material could be made of a relatively stiff material and the components that are made of a relatively stiff material could be made of a relatively flexible, soft material.

The prosthetic devices of the above embodiments can be inserted between the facets of adjacent vertebrae, rather than the spinous processes;

The prosthetic devices of the above embodiments can be implanted between body portions other than vertebrae.

The prosthetic devices of the above embodiments can be inserted between two vertebrae following a discectemy in which a disc between the adjacent vertebrae is removed, or corpectomy in which at least one vertebrae is removed.

The spatial references made above, such as "under", "over", "between", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A prosthetic device for insertion between adjacent vertebrae, the device comprising:
   a first member adapted to extend between the vertebrae;
   two second members, each supported by the first member;
   wherein the first member is a body member having two grooves formed in opposite faces thereof and wherein the two second members each comprise an insert having a substantially U-shaped cross section, the U-shaped cross-section of each second member being formed in part by two spaced apart legs, the legs being insertable in the first and second grooves;
   wherein the first member is formed of a relatively flexible material compared to the second members and the second members are formed of a relatively stiff material compared to the first member.

2. The device of claim 1 wherein the grooves extend across a width of the first body member and wherein each of the inserts is insertable into one of the grooves.

3. The device of claim 1 wherein the body member has two notches at its respective ends for receiving a portion of the two vertebrae, respectively.

4. The device of claim 1 wherein each of the two second members includes a gap separating the two spaced apart legs, the first member extending into the gap.

5. The device of claim 1 wherein the two spaced apart legs of each second member include a first leg and a second leg, the first leg of each second member extending in one of the grooves and the second leg of each second member extending in another of the grooves.

6. A prosthetic device for insertion between adjacent vertebrae, the device comprising:
   a first member having a first and second end and adapted to extend between the vertebrae, the first member having an outer surface and having first, second, third, and fourth sides extending between the ends, the first and third sides being opposite each other and the second and fourth sides being opposite each other, the first member having a notch formed in the first end for receiving a portion of one of the vertebrae, the notch extending from the first side to the third side of the first member, the outer surface including a rectangular-shaped opening formed therethrough, the rectangular-shaped opening being an opening of a rectangular-shaped channel, the rectangular-shaped channel having a planar surface extending from the second to the fourth side of the first member;
   at least one second member supported by the first member, the at least one second member shaped to at least partially pass through the rectangular-shaped opening;
   wherein the first member is formed of a relatively flexible material compared to the second member and the second member is formed of a relatively stiff material compared to the first member.

7. The device of claim 6 wherein the vertebrae portion is a spinous process.

8. The device of claim 6 wherein the first member has two notches at its respective ends for receiving the spinous processes of the adjacent vertebrae.

9. The device of claim 6 wherein, the second member is replaceable by a member with a stiffness that differs from the stiffness of the second member.

10. The device of claim 6 wherein the second member is an insert that extends in the channel.

11. The device of claim 10 wherein the first member has two notches at its respective ends for receiving a portion of the two vertebrae, respectively.

12. A prosthetic device for insertion between adjacent vertebrae, the device comprising:
   a first member adapted to extend between the vertebrae, the first member having an outer surface and having first, second, third, and fourth sides extending between the ends, the first and third sides being opposite each other and the second and fourth sides being opposite each other, the first member having a notch formed in a first end for receiving a portion of one of the vertebrae, the notch extending from the first side to the third side of the first member, the outer surface including a rectangular-shaped opening formed therethrough, the rectangular-shaped opening being an opening of a rectangular-shaped channel, the rectangular-shaped channel having a planar surface extending from the second to the fourth side of the first member;
   at least one second member supported by the first member, the at least one second member shaped to at least partially pass through the rectangular-shaped opening;
   wherein at least a portion of the at least one second member disposed in the rectangular-shaped channel has a rectangular-shaped cross-section;
   wherein the first member is formed of a relatively flexible material compared to the second member and the second member is formed of a relatively stiff material compared to the first member.

13. A prosthetic device for insertion between adjacent vertebrae, the device comprising:
   a first member being a one-piece integral body adapted to extend between the vertebrae, the first member having an outer surface and having first, second, third, and fourth sides extending between the ends, the first and third sides being opposite each other and the second and fourth sides being opposite each other, the first member having a notch formed in a first end for receiving a portion of one of the vertebrae, the notch extending from the first side to the third side of the first member, the outer surface including a rectangular-shaped opening formed therethrough, the rectangular-shaped opening being an opening of a rectangular-shaped channel, the rectangular-shaped channel having a planar surface extending from the second to the fourth side of the first member;

at least one second member supported by the first member, the at least one second member shaped to at least partially pass through the rectangular-shaped opening;

wherein the first member is formed of a relatively flexible material compared to the second member and the second member is formed of a relatively stiff material compared to the first member.

14. An implantation method between two adjacent vertebrae, the method comprising:

providing a first member having two grooves formed in opposite faces thereof; selecting two second members from a plurality of second members having different relative stiffnesses; the two second members each being an insert having a substantially U-shaped cross section that is insertable in the grooves;

supporting the second members by the first member to form a prosthesis; and implanting the prosthesis between the vertebrae.

15. The method of claim 14 wherein the grooves extend across a width of the first body member and wherein the method further comprises inserting the two second members into one of the grooves.

16. The method of claim 14 further comprising forming two notches at the respective ends of the first member for receiving a portion of the two vertebrae, respectively.

17. An implantation method between two adjacent vertebrae, the method comprising:

providing a first member;

selecting a second member from a plurality of second members having different relative stiffnesses;

supporting the second member by the first member to form a prosthesis; wherein the step of supporting comprises forming two grooves formed in opposite faces of the first member and wherein the second member is at least one insert having a substantially U-shaped cross section that is insertable in the grooves;

implanting the prosthesis between the vertebrae;

replacing the second member with a member of a material having a different stiffness than the material of the second member;

wherein the first member is formed of a relatively flexible material compared to the second member and the second member is formed of a relatively stiff material compared to the first member.

18. An implantation method between two adjacent vertebrae, the method comprising:

providing a first member;

selecting a second member from a plurality of second members having different relative stiffnesses;

supporting the second member by the first member to form a prosthesis;

implanting the prosthesis between the vertebrae;

subsequently to said implanting, replacing the second member with one of the plurality of second members formed of a material having a different stiffness than the material of the second member;

wherein the first member is formed of a relatively flexible material compared to the second member and the second member is formed of a relatively stiff material compared to the first member.

19. The method of claim 18 further comprising forming at least one notch in the first member for receiving a portion of one of the vertebrae.

20. The method of claim 19 wherein the vertebrae portion is a spinous process.

21. The method of claim 19 further comprising forming two notches at the respective ends of the first member for receiving the spinous processes of the adjacent vertebrae.

22. The method of claim 18 further comprising forming a channel in the first member and wherein supporting the second member by the first member comprises inserting the second member in the channel.

23. The method of claim 22 further comprises forming notches at the respective ends of the first member for receiving a portion of the two vertebrae, respectively.

24. The method of claim 18 wherein there are two second members and the method further comprises forming a channel in the first member and inserting each of the second members in the channel.

25. The method of claim 18 wherein the step of supporting comprises introducing the second member into a receiving feature on the first member, the first member and the second member being shaped so that the second member is introducible in only one axial direction.

* * * * *